United States Patent [19]

Hampele et al.

[11] Patent Number: 5,713,927
[45] Date of Patent: Feb. 3, 1998

[54] DEFIBRILLATING DEVICE EQUIPPED WITH A PLURALITY OF CONNECTOR/ELECTRODE ASSEMBLIES OF DIFFERENT TYPES

[75] Inventors: Roland Hampele, Haguenau; Michel Kraemer, Durrenbach, both of France

[73] Assignee: "O.D.A.M." Office de Distribution d'Appareils Medicaux (SA), Wissenbourg, France

[21] Appl. No.: 488,780

[22] Filed: Jun. 8, 1995

[30] Foreign Application Priority Data

Jun. 9, 1994 [FR] France .................................. 94 07212

[51] Int. Cl.⁶ .................................................. A61N 1/39
[52] U.S. Cl. .................................................. 607/5; 607/63
[58] Field of Search ........................... 607/5, 142, 63

[56] References Cited

U.S. PATENT DOCUMENTS 4,837,488 6/1989 Donahue .
5,181,858 1/1993 Matz et al. .
5,441,520 8/1995 Olsen et al. ........................... 607/5

FOREIGN PATENT DOCUMENTS

0 353 341 2/1990 European Pat. Off. .
WO93/16759 9/1993 WIPO .

Primary Examiner—Scott M. Getzow
Attorney, Agent, or Firm—Young & Thompson

[57] ABSTRACT

Defibrillating device equipped with a plurality of connector/electrodes assemblies of different types. Defibrillating device equipped with a plurality of connector/electrodes assemblies of different types, having each at least a connector cable and adapted to be plugged in, in a removable and interchangeable manner, to the casing of the device at a single connection site equipped with a fixed complimentary connector, all of the control (13, 13') and, preferably, adjustment devices (17) of the functioning of the defibrillating device (1) being mounted on the connector (8)/electrodes (9, 9') assemblies, each type of which is intended for a class of authorized user and/or specific application(s), the casing (2) of the defibrillating device (1) having only indicator and/or display devices (2'), and preferably, no control or adjustment device.

7 Claims, 8 Drawing Sheets

FIG-3A

DEFIBRILLATING DEVICE EQUIPPED WITH A PLURALITY OF CONNECTOR/ELECTRODE ASSEMBLIES OF DIFFERENT TYPES

The present invention relates to devices for the treatment of cardiac dysfunctions, notably in the reanimation field, and has for its object a defibrillating device equipped with a plurality of different types of connector/electrode assemblies.

There already exists a certain number of defibrillators, constituted by a casing containing the different functional modules for the charging of the capacitor, for control and, if the need arises, for analysis, different connector/electrodes assemblies, each comprising at least one connecting cable, and being able to be plugged into, in a removable and interchangeable manner, the casing of said device at a single connecting site equipped with a specially adapted complimentary fixed adapter.

Among these electrodes, one finds, on the one hand, external use electrodes such as paddle electrodes or large adhesive electrodes and, on the other hand, internal use surgical electrodes, in the shape of spoons, to be applied directly to the heart.

Currently, the control of these defibrillating devices is effectuated by means of buttons or control keys disposed on the casing of the device, except for the paddle electrodes whose triggering buttons are disposed on the electrodes themselves.

Moreover, an energy selector, allowing the user to determine the level of the charge, as a function of the type of electrodes and in the judgment of the practitioner, is also generally provided on the casing of said device.

Additionally, said defibrillating devices can function either in manual mode (determination of the level of energy and triggering of the charge by action from the user), or in semi-automatic mode (determination of energy, triggering of the charge, and authorization of triggering of the defibrillation controlled by the device itself), this as a function of the level of qualification of the user, and necessitating, from this fact, a mode switch, often integrated in the energy selector in the form of a supplementary switching position of said selector, corresponding to said semi-automatic mode.

However, it is necessary to be able to interdict a utilization with manual control and adjustment of the defibrillation devices, notably in the hospital environment, for persons insufficiently qualified, not trained, or for persons only used to semi-automatic use, from a lack of practice or instruction.

To attempt to establish a selective utilization of said defibrillating devices, it has been proposed to equip these latter with locks or authorization codes to access the control and manual adjustment mode.

However, these solutions can be impossible to implement because of the singular nature of the key of the lock, or because of the limited number of people who can use a given defibrillating device, not allowing a qualified person, not knowing the code or not having the above-cited key, to use any defibrillating device in manual mode.

Moreover, the mode of functioning and the energy adjustment possibilities as a function of the connected electrodes do not always appear clearly and in a readily apparent manner on the casing of the defibrillating device and, given the plurality of the adjustment and control devices present, as well as their dispersed placement or placement in the casing of the device, can lead to delays or harmful loss of time.

An object of the present invention is to overcome all of the above-cited disadvantages.

To this end, it has for its object a defibrillating device equipped with a plurality of connector/electrodes assemblies of different types, each comprising at least one connecting cable and said assemblies being able to be plugged into, in a moveable and interchangeable manner, the casing of said device at a single connecting site provided with a specially adapted complimentary fixed connector, characterized in that the control and preferably the adjustment of functioning devices of said defibrillating device are mounted on the connector/electrodes assemblies, each type of which is assigned a type of authorized users and/or specific application(s), the casing of the defibrillating device only comprising signaling and/or display devices, and preferably, no control or adjustment device.

The invention will be better understood thanks to the description below, which relates to preferred embodiments, given as non-limiting examples, and explained with reference to the accompanying schematic drawings, in which:

FIG. 6 is an electrical schematic of the connector depicted in FIG. 5;

According to the invention, as shown in the attached FIGS. 1–7, the defibrillating device 1 is implemented in such a manner that all the means for control 13, 13', 18, 21 and, preferably, for adjustment 17 of functioning devices of said defibrillating device 1 are mounted on the connector 8/electrodes 9, 9' assemblies, each type of which is assigned to a type of authorized user and/or to specific application(s), the casing 2 of the defibrillating device 1 comprising only signaling and/or display devices 2', and preferably, no control or adjustment devices.

Each type of connector 8/electrodes 9, 9' assemblies being intended for a well defined application and treatment, it is advantageous that the defibrillating device 1 presents as many different modes of functioning, of adjustment and/or semi-automatic, or manual control, as there are different types of connector 8/electrodes 9, 9' assemblies, the appropriate mode of functioning being automatically selected upon plugging in the connector 8 of the connector 8/electrodes 9, 9' assembly in question in the fixed connector 7 of the casing 2 of the defibrillating device 1.

In this manner, as soon as the connector 8/electrodes 9, 9' assembly is put in place by plugging in to the fixed connector 7 (whose placement or the region around the casing can have an indexed configuration complimentary to that of the casing 10 of the connector 8 in such a manner as to facilitate the speedy and correct assembly of said connectors 7 and 8), the computer unit controlling the defibrillating device can select and follow the preprogrammed operative protocol adapted to the type of connector 8/electrodes 9, 9' assembly plugged in, and thus to the envisaged application, and to the type of user manipulating said defibrillating device.

Figure 4:
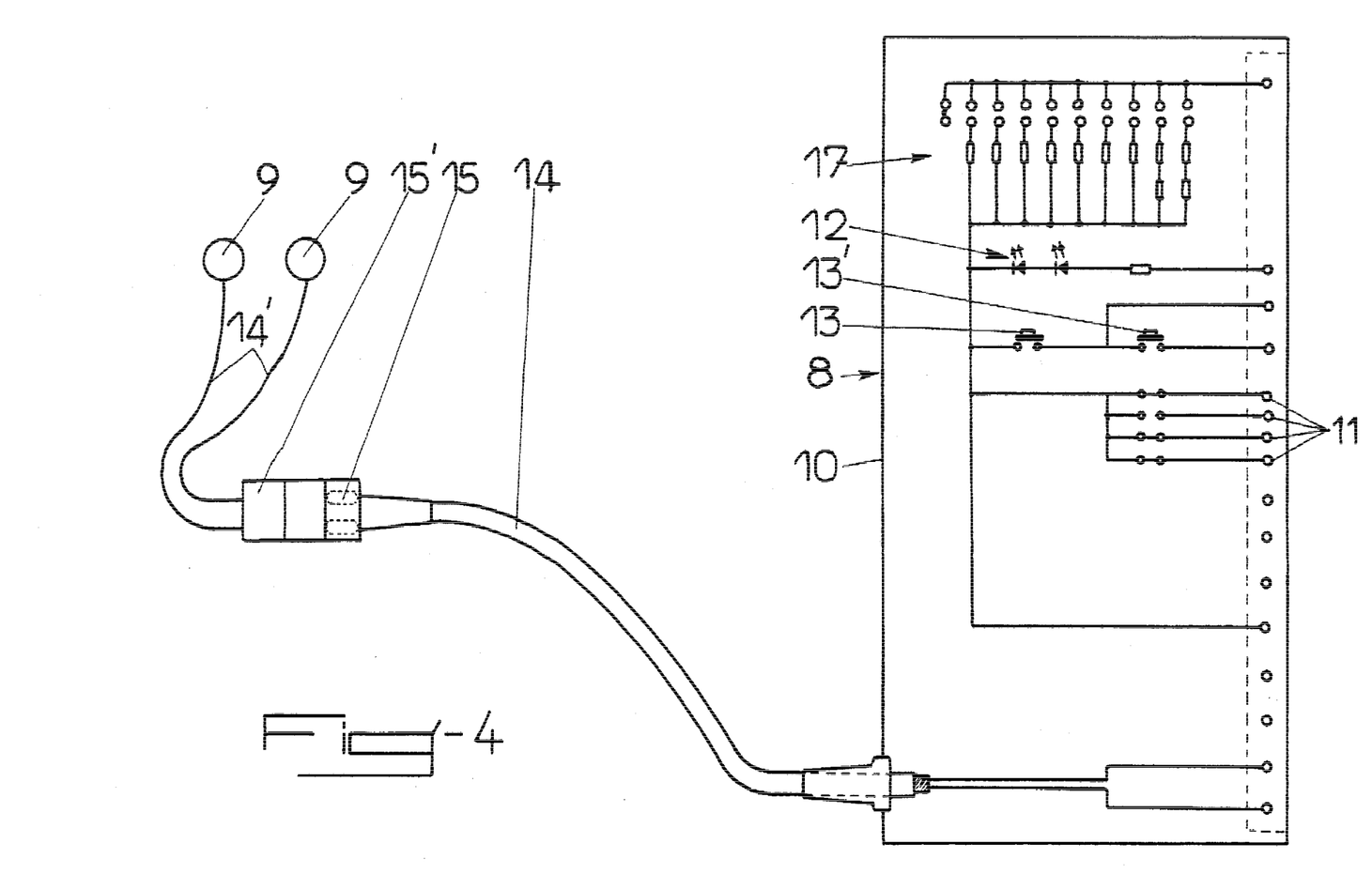
FIG. 4 is an electrical schematic of the connectors depicted in FIGS. 3A and 3B.
Figure 8:
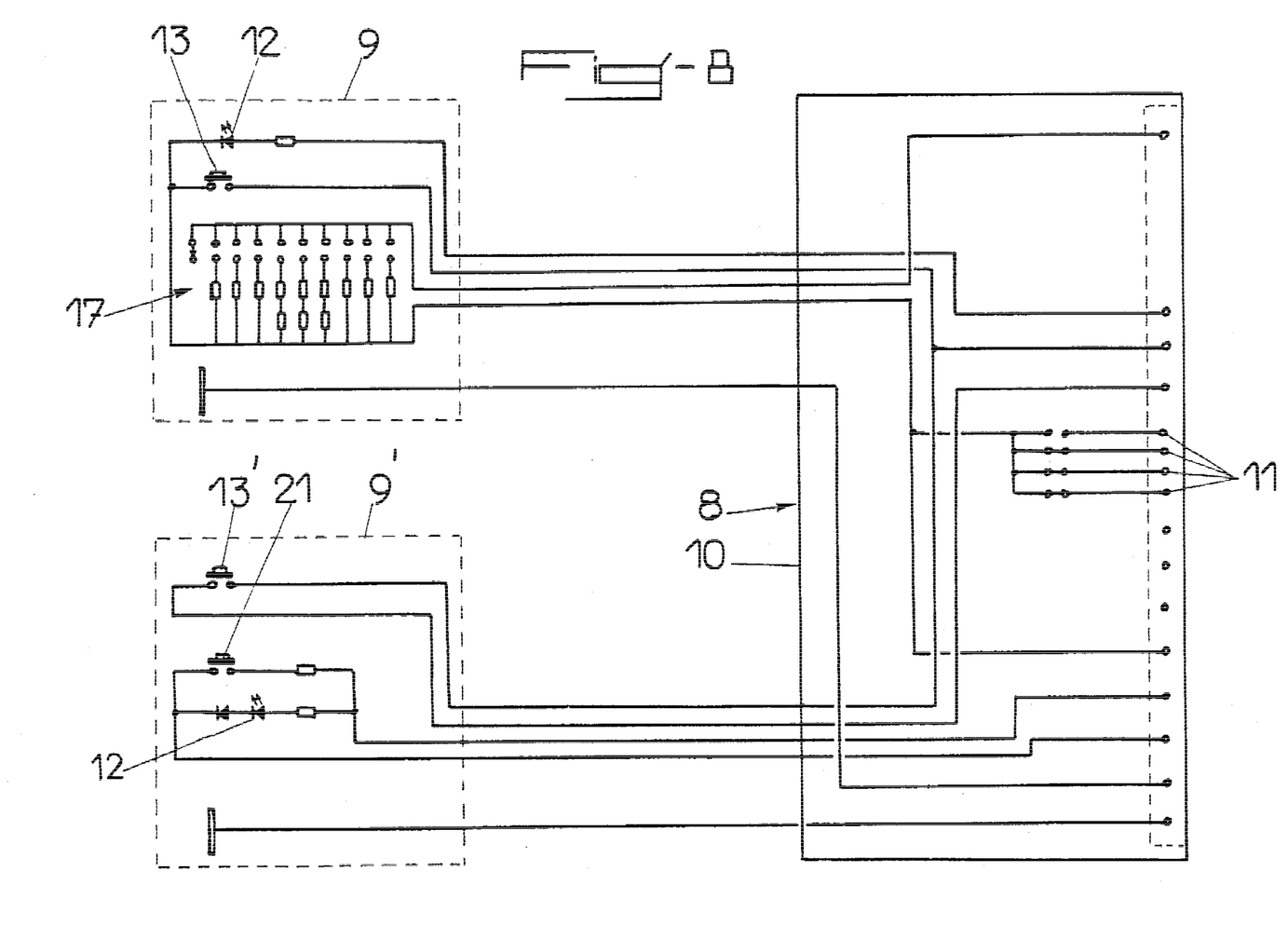

As FIGS. 4, 6 and 8 of the attached drawings show, each connector 8 comprises a means for its recognition from the casing 2 of the defibrillating device 1 upon its plugging in, specific to the type of connector 8/electrodes 9, 9' assembly to which it belongs, said recognizing means consisting of a definition of the state of at least one connection point 11 of said connector 8, advantageously during the period of plugging in this latter in the casing 2 of the defibrillator device 1.

According to a characteristic of the invention, represented in part in FIGS. 4, 6 and 8 of the attached drawings, the recognizing means advantageously consist of a logical coding by fixing the states of specific connection points 11 of the connector 8, each binary code thus obtained identifying in a unique manner each type of connector 8/electrodes 9, 9' assembly and indicating automatically to the defibrillating device 1, on the one hand, the occurrence of a plugging in of an authorized connector 8/electrodes 9, 9' assembly and, on the other hand, the type of assembly plugged in and the corresponding mode of functioning.

In this manner, the presence of four connection points 11 allows to individually define, by connecting three connection points 11, and leaving unconnected a fourth connection point 11, each of the four types of assembly to be plugged in by the generation of the codes 1000, 0100, 0010, and 0001.

Moreover, the code 1111 could be interpreted as indicating the absence of connection of all connector/electrode assemblies, and cause the defibrillating device 1 to be put in a ready state, all codes other than those mentioned above would correspond to an abnormal state, to a faulty connection, or to some malfunction and will, as soon as it is identified, result in the triggering of an alarm signal.

As FIGS. 4, 6 and 8 of the attached drawings also show, each connector 8/electrodes 9, 9' assembly comprises at least an indicator 12 signaling the end of the charging phase and the authorization to discharge and two buttons 13, 13' or control keys connected to each other, for example by series connection, allowing the triggering of the defibrillation discharge by simultaneously depressing these latter.

Figure 1:
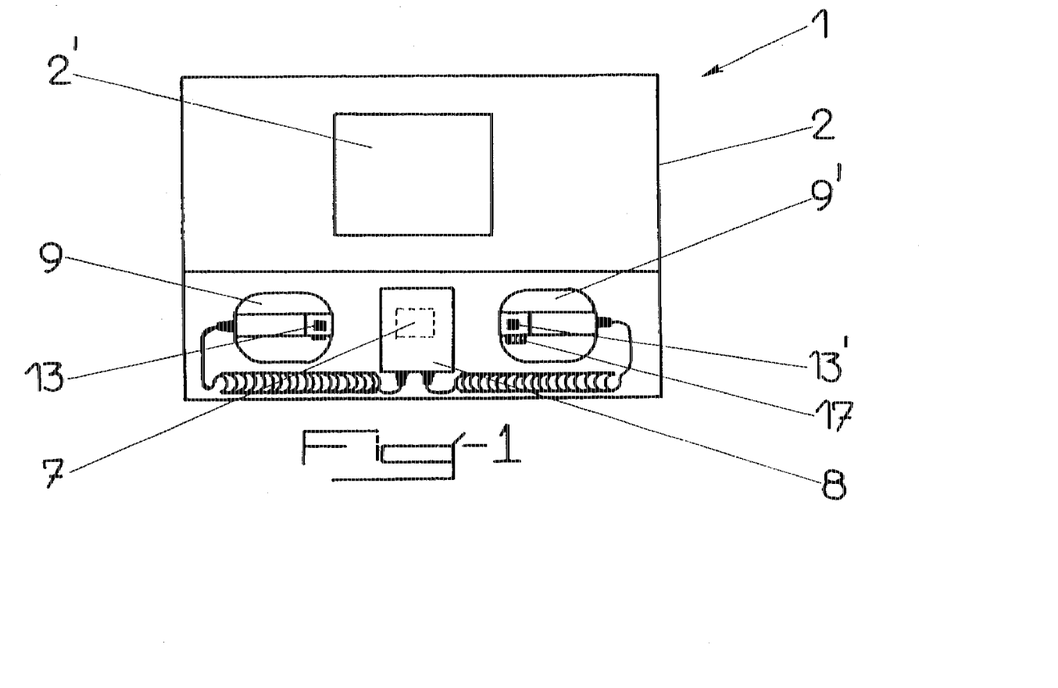
FIG. 1 is a top view of the defibrillating device according to the invention.
Figure 2:
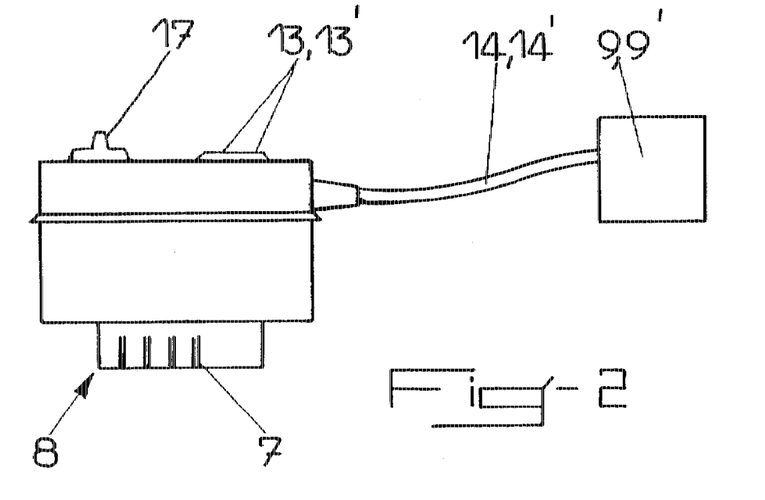
FIG. 2 is a lateral elevation schematic view of a connector/electrodes assembly according to the present invention.
Figure 3A:
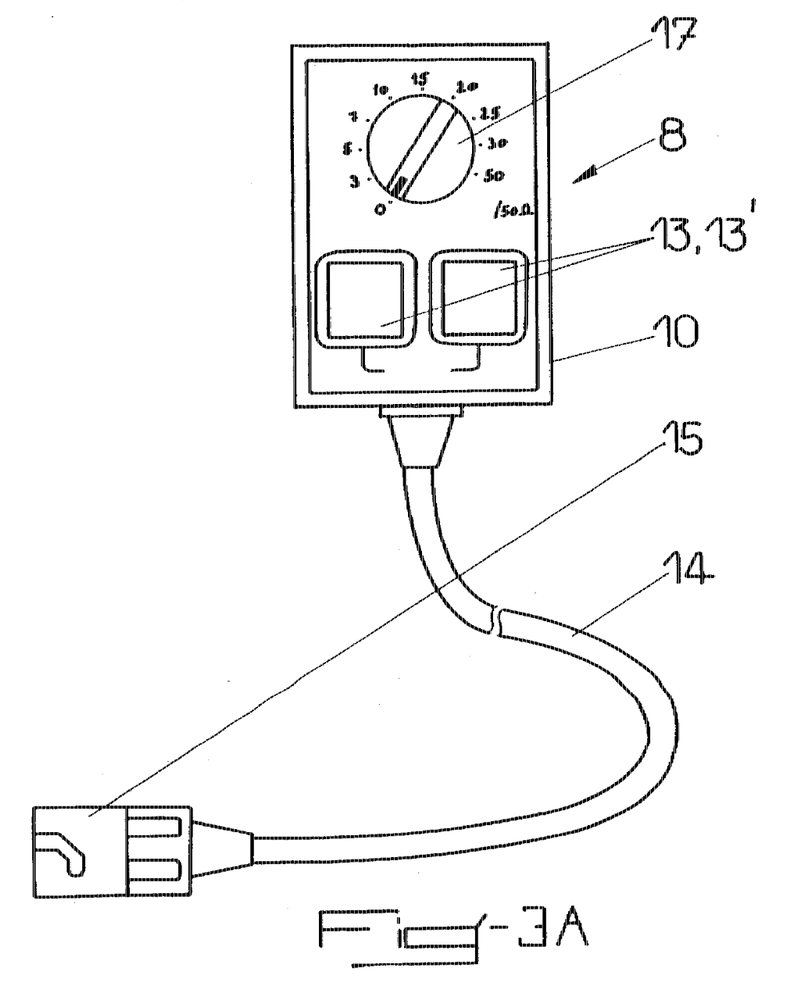
FIGS. 3A and 3B are front elevation views of the connectors according to the invention and adapted to be assembled, respectively, with internal electrodes, or adhesive electrodes.
Figure 3B:
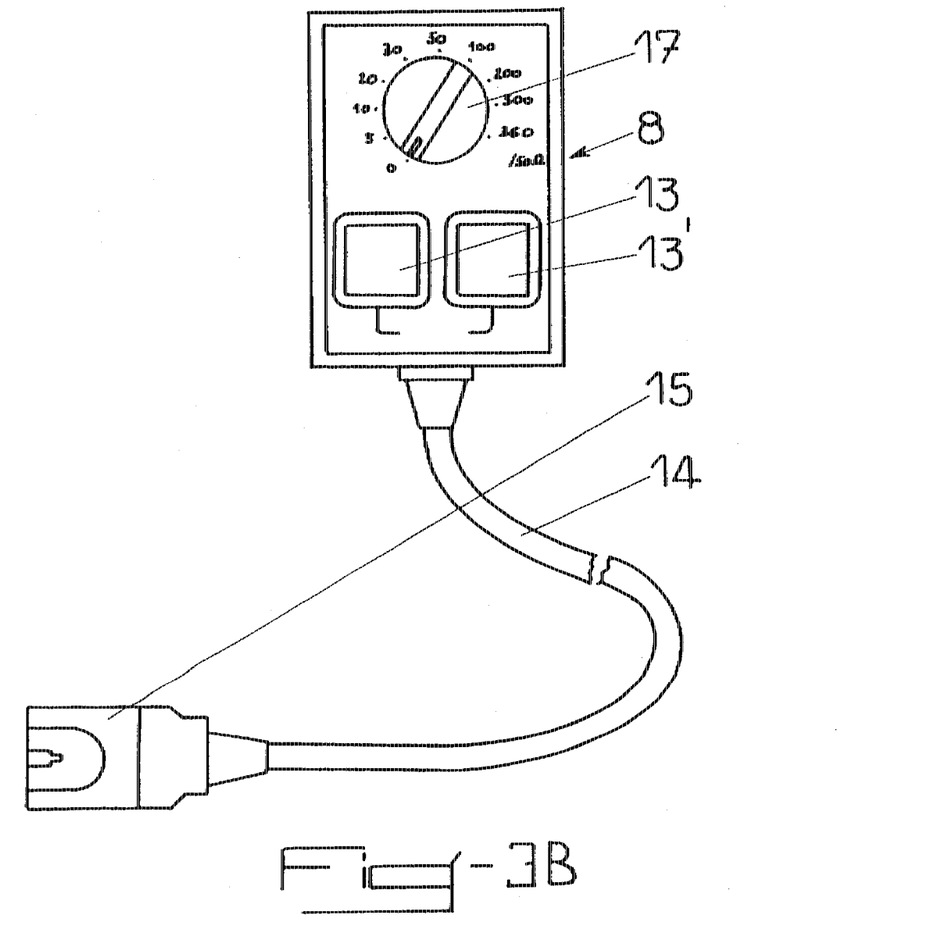

According to a first variant of the embodiment of the invention, represented in FIGS. 3A, 3B and 4 of the attached drawings, the assemblies of connector 8/electrodes 9, 9' comprise, within the framework of implementation of the electrodes 9, 9' of the internal or adhesive type, a connecting cable in two portions, 14 and 14', connectable to each other in a removable manner by a connecting device constituted by a male connector 15/female connector 15' pair specific to the type of electrodes 9, 9' to connect to the connector 8, the casing 10 enclosing this latter comprising at least a discharge authorization indicator 12 and two buttons 13, 13' or keys connected, for example, in series, controlling the defibrillation discharge.

This setup allows to separate the part of the assembly comprising the electrodes 9, 9' from the part comprising the connector 8, permitting in this manner a sterilization treatment or single use of said electrodes 9, 9' intended to be in contact with body of the patient.

When a person qualified and practiced in carrying out the defibrillation with manual control and adjustment wants to carry out a defibrillation with the internal or adhesive electrodes 9, 9', he or she will be able to implement a connector 8/electrodes 9, 9' assembly of the type described above and whose casing 10 of the connector 8 comprises an energy selector 17 variable stepwise, the triggering of the charge of the defibrillating device 1 being controlled by pressure on one of the two buttons 13, 13' or keys coupled between themselves (see FIGS. 3A, 3B and 4).

The structure and the electrical configuration of the connectors 8 used in association with the internal or adhesive electrodes 9, 9' are identical, as an analysis of FIG. 4 reveals and a comparison, between themselves, of FIGS. 3A and 3B, the only difference residing in the terracing of the energy levels of the charge, as well as in the maximum available values.

Indeed, for a connector 8 intended to be coupled with internal electrodes 9, 9', the maximum authorized, and thus selectable energy (generally 50 Joules), will be clearly less than that authorized to be selected and delivered by the connector 8 associated with the large adhesive electrodes 9, 9' intended to be placed on the skin of a patient (generally 360 Joules).

Providing the specific connectors 15, 15', on the one hand, to the assemblies of internal connector 8/electrodes 9, 9' and, on the other hand, to the assemblies of adhesive connector 8/electrodes 9, 9' avoids all reversals at the moment of associating the connector 8 with the electrodes 9, 9' of the corresponding type.

Figure 5:
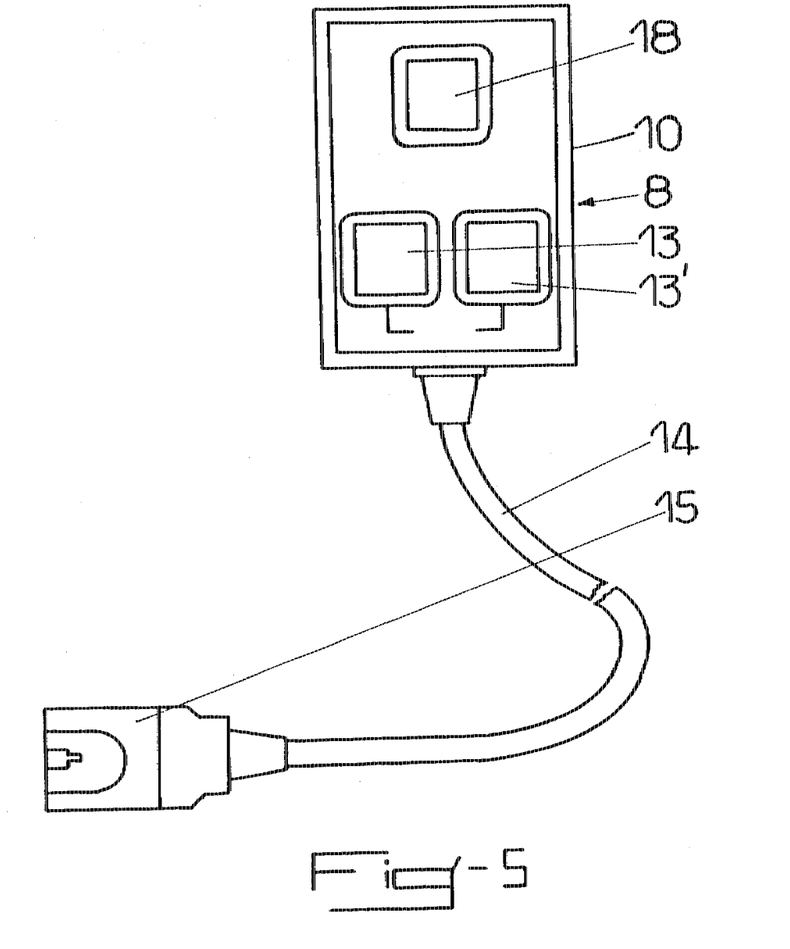
FIG. 5 is a front elevation view of a connector according to the invention for a semi-automatic functioning of the defibrillating device, adapted to be assembled with adhesive electrodes.

To carry out defibrillation operations, particularly with the adhesive electrodes 9, 9', by unqualified personnel or those not possessing the training or the experience necessary for an entirely manual operation, it is possible to provide, as FIGS. 5 and 6 of the attached drawings particularly show, connector 8/electrodes 9, 9' assemblies constituted by two parts assembled in a removable manner as previously indicated (specific connectors 15, 15'—connecting cable in two parts), but whose casing 10 of the connector 8 no longer comprises the energy selector 17 and comprises, in replacement, a button or an automatic triggering key for an electrocardiogram plot, from the defibrillation electrodes 9, 9' previously attached to the patient, associated with a measurement and analysis phase signalization indicator 19.

Said electrocardiogram is analyzed by said defibrillating device 1 which, depending on the results, authorizes or not the carrying out of the defibrillation, by triggering, preferably automatically, the charging operation, and determines, in association if desired with additional data (weight of the patient, age of the patient or standard protocols or recommendations, etc.) furnished to said device 1, the value of the charge or the values of successive charges.

Figure 7:
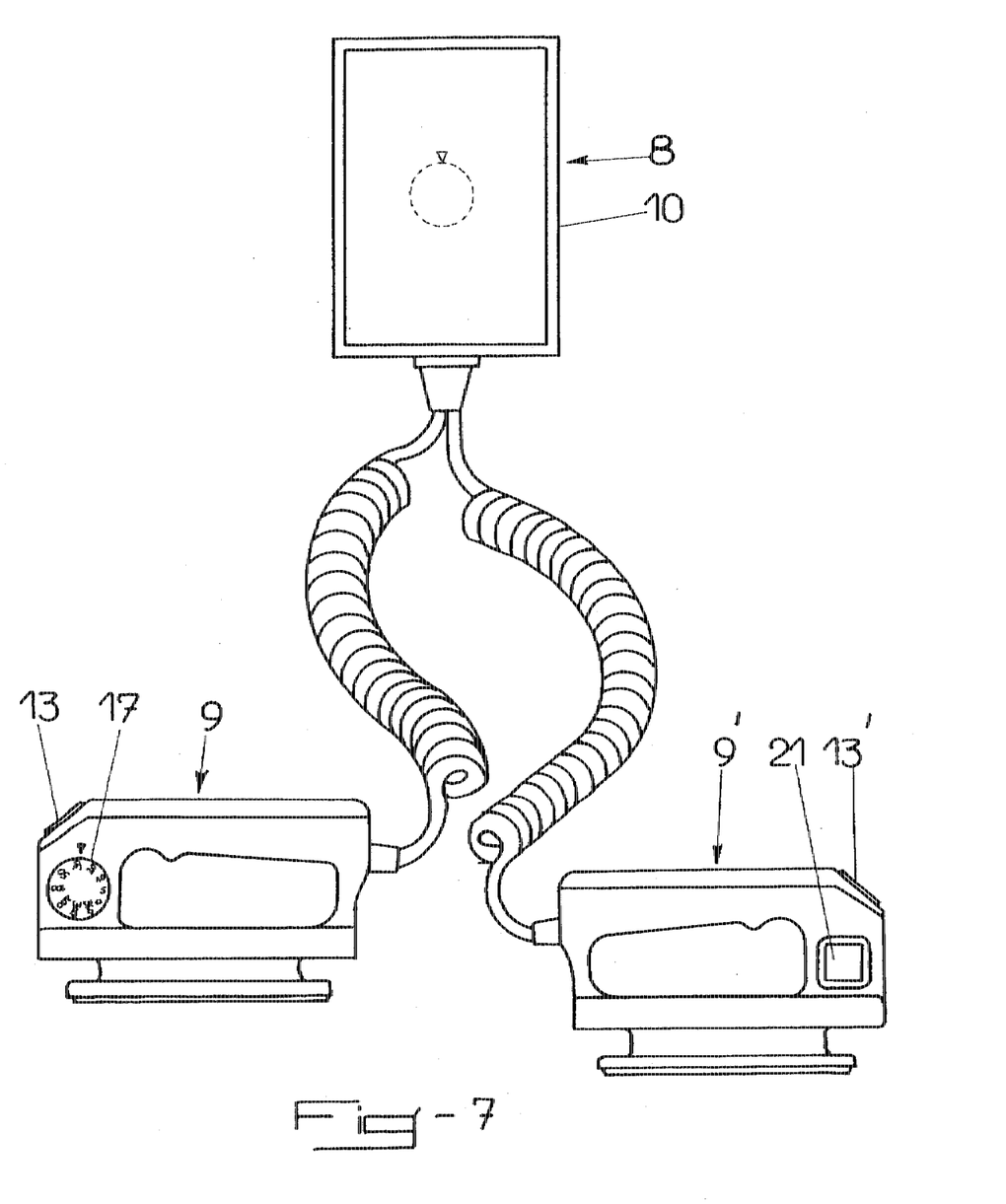
FIG. 7 is a front elevation view of a connector/electrodes assembly according to the present invention comprising paddle electrodes, and, FIG. 8 is an electrical schematic of the connector/electrodes assembly depicted in FIG. 7.

According to a second embodiment of the invention, represented in FIGS. 7 and 8 of the attached drawings and described within the framework of the assemblies of connector 8/electrodes 9, 9' comprising paddle electrodes, it is intended that the casings of these latter additionally comprise a discharge authorization indicator 12 and two keys or buttons 13, 13' acting independently for the control of the charging and being connected together for controlling the discharge, an energy selector 17 variable stepwise, and a key or triggering button 21 of an electrocardiogram plot mounted on one or the other of said casings 20, 20' of the electrodes 9, 9'.

However, as a variation, the energy selector may also be mounted on the casing of the connector 8 (see phantom lines in FIG. 7).

Thanks to the invention, it is therefore possible to effect a separation between people qualified in manual mode defibrillations and people authorized to carry out only defibrillations in semi-automatic mode, by allocating one or many of the connector 8/electrodes 9, 9' assemblies to each person susceptible to carry out a defibrillation. Moreover, each connector/electrodes assembly is clearly identifiable by its appearance and its control and/or adjustment devices with which it is equipped, this identification also being optionally facilitated by the choice of a specific color for each assembly. Additionally, the location of the control and/or adjustment devices on the connector/electrode assemblies allows the user to permanently work in an identical control and adjustment context and to be able to use any defibrillating device, even possibly other types, having the corresponding fixed connector and the associated functioning mode, wherever said device is implemented.

It is to be understood that the invention is not limited to the embodiment described and represented in the attached drawings. Modifications remain possible, notably with respect to the configuration of the various elements, or by substitution of equivalent techniques, without thereby departing from the scope of protection of the invention.

We claim:

1. Defibrillating system comprising a defibrillating device and a plurality of connector/electrodes assemblies of different types, each of which comprising at least one connecting cable adapted to be removably and interchangeably connected to a casing of said defibrillating device at a unique connection site equipped with a fixed mating connector, wherein all control (13, 13', 18, 21) and functioning adjustment devices (17) of said defibrillating device (1) are mounted on the connector (8)/electrodes (9, 9') assemblies, the casing (2) of said defibrillating device (1) comprising only display devices, and no control or functioning adjustment devices, wherein a first type of said plurality of connector/electrode assemblies comprises a first control assembly with a display indicating discharge authorization, a manually operated variable energy selector, and two control buttons for controlling the defibrillating discharge at the manually selected energy level, wherein a second type of said plurality of connector/electrode assemblies comprises a second control assembly without a manually operated variable energy selector and including a display indicating discharge authorization, a switch for requesting automatic determination by said defibrillating device of an energy level, and two control buttons for controlling the defibrillating discharge at the automatically selected energy level, and wherein each of said first and second connector/electrode assemblies further comprise electrodes selected from the group consisting of paddle electrodes, internal electrodes and adhesive electrodes.

2. Defibrillating system according to claim 1, further comprising as many different functioning modes as there are different types of connector (8)/electrodes (9, 9') assemblies, a particular mode of functioning being selected automatically upon connecting a connector (8) of the plurality of connector (8)/electrodes (9, 9') assemblies to said fixed mating connector (7) of the casing (2) of the defibrillating device 1.

3. Defibrillating system according to claim 2, wherein each connector (8) of said plurality of connector (8)/electrodes (9, 9') assemblies comprises means for identifying itself to the casing (2) of the defibrillating device (1) upon its connection thereto, said identification means being specific to the type of connector (8)/electrodes (9, 9') assembly to which said connector (8) belongs, said identification means consisting of a state of at least one connection point (11) of said connector (8), when connecting said connector (8) in the casing (2) of the defibrillating device 1.

4. Defibrillating system according to claim 3, wherein said identification means generates a binary code by setting the states of said connection points (11) of the connector (8), each binary code thus obtained identifying, in a unique manner, each type of connector (8)/electrodes (9, 9') assembly and automatically indicating to the defibrillating device (1) a connection of the connector (8)/electrodes (9, 9') assembly and the type of connector (8)/electrodes (9, 9') assembly connected in a corresponding functioning mode.

5. Defibrillating system according to claim 1, wherein each connector (8)/electrodes (9, 9') assembly of said plurality of connector (8)/electrodes (9, 9') assemblies comprises at least an indicator (12) signalling an end of a charging phase and a discharge authorization, and two buttons (13, 13') or control keys connected to each other in series, allowing a triggering of a defibrillating discharge by simultaneous depression of said two buttons (13, 13') or control keys.

6. Defibrillating system according to claim 1, wherein said switch is for triggering automatic generation of an electrocardiogram obtained via defibrillation electrodes (9, 9') adapted to be attached to the patient, said switch being associated with a display (19) signalling a measurement and analysis phase, said electrocardiogram being analyzed by said defibrillating device (1) which, depending on results of said electrocardiogram, decides whether to authorize a carrying out of a defibrillation by automatically triggering a charging operation and which determines one of a value of single charge and values of successive charges on the basis of said results and optional supplementary data input to said defibrillating device.

7. The system of claim 1, wherein said paddle electrode houses one of said first and second control assemblies, and wherein said internal and adhesive electrodes are separate from said first and second control assemblies.

\* \* \* \* \*